(12) United States Patent
Havenga et al.

(10) Patent No.: US 11,619,622 B2
(45) Date of Patent: Apr. 4, 2023

(54) DRILLING MUD MANAGEMENT SYSTEM AND METHOD

(71) Applicant: AUSTRALIAN MUD COMPANY PTY LTD, Balcatta (AU)

(72) Inventors: Frans Christiaan Havenga, Hamersley (AU); Storm Kyle Burnham, Myersdal (ZA); Shaun David Wilson, Salt Lake City, UT (US)

(73) Assignee: Australian Mud Company Pty Ltd, Balcatta (AU)

( * ) Notice: Subject to any disclaimer, the term of this patent is extended or adjusted under 35 U.S.C. 154(b) by 387 days.

(21) Appl. No.: 16/643,943

(22) PCT Filed: Sep. 10, 2018

(86) PCT No.: PCT/AU2018/050974
§ 371 (c)(1),
(2) Date: Mar. 3, 2020

(87) PCT Pub. No.: WO2019/046904
PCT Pub. Date: Mar. 14, 2019

(65) Prior Publication Data
US 2020/0371084 A1    Nov. 26, 2020

(30) Foreign Application Priority Data

Sep. 8, 2017    (AU) ................................ 2017903659

(51) Int. Cl.
*G01N 33/28* (2006.01)
*E21B 21/06* (2006.01)
(Continued)

(52) U.S. Cl.
CPC ....... *G01N 33/2823* (2013.01); *E21B 21/062* (2013.01); *G01F 23/292* (2013.01);
(Continued)

(58) Field of Classification Search
CPC ........ E21B 21/062; E21B 21/08; E21B 44/00; E21B 21/01; E21B 47/00; E21B 49/08;
(Continued)

(56) References Cited

U.S. PATENT DOCUMENTS

| 4,557,142 A | 12/1985 | Hensley et al. | |
|---|---|---|---|
| 5,844,147 A * | 12/1998 | Fiedler | G01N 1/40 73/863.21 |

(Continued)

FOREIGN PATENT DOCUMENTS

| EP | 3182119 A1 * | 6/2017 |
|---|---|---|
| GB | 2401944 A | 11/2004 |
| WO | 2012025840 A2 | 3/2012 |

*Primary Examiner* — John Fitzgerald
*Assistant Examiner* — Gedeon M Kidanu
(74) *Attorney, Agent, or Firm* — Felix L. Fischer (57) ABSTRACT

An automated batch sampling drilling mud management system (1) includes a portable mud measurement system (10) and a communications system (120). The portable mud measurement system (10) has one or more measurement devices (14) arranged to measure at least one property and/or characteristic of drilling mud; and a pumping system (16) arranged to pump a batch sample of drilling mud from a supply of drilling mud to the one or more measurement devices. The pumping system (16) is also able to subsequently flush the batch sample of drilling mud from the one or more measurement devices (14). The communications system (120) enables bidirectional communications between the mud management system (10) and a remote location to enable transfer of data therebetween and the exertion of control from the remote location to the mud management system (10).

18 Claims, 5 Drawing Sheets

(51) Int. Cl.
*G01F 23/292* (2006.01)
*G01N 1/14* (2006.01)
*G01N 9/26* (2006.01)
*G01N 11/00* (2006.01)

(52) U.S. Cl.
CPC .............. *G01N 1/14* (2013.01); *G01N 9/26* (2013.01); *G01N 11/00* (2013.01)

(58) Field of Classification Search
CPC ...... E21B 49/088; G06F 16/00; G01F 23/292; G01N 1/14; G01N 11/00; G01N 33/2823; G01N 9/26
See application file for complete search history.

(56) References Cited

U.S. PATENT DOCUMENTS

| | | | |
|---|---|---|---|
| 8,392,121 B2 * | 3/2013 | Zamora | G01N 33/2823 702/50 |
| 10,385,636 B2 * | 8/2019 | Midlang | G01N 33/2823 |
| 10,465,511 B2 * | 11/2019 | Watson | E21B 21/01 |

\* cited by examiner

DRILLING MUD MANAGEMENT SYSTEM AND METHOD

REFERENCES TO RELATED APPLICATIONS

This application is a national stage filing under 35 U.S.C. 371 and claims priority of International Application serial no. PCT/AU2018/050974 having an international filing date of 10 Sep. 2018 which in turn claims priority of Australian patent application serial no. 2017903659 filed on 8 Sep. 2017, the disclosures of which are incorporated herein by reference.

TECHNICAL FIELD

The present disclosure relates to a drilling mud management system and method. The system and method have application in the field of ground drilling where drilling mud is used or required for various purposes including not limited to downhole pressure control, hole stabilisation, lubrication, flushing of drill cuttings and downhole temperature control.

BACKGROUND ART

Drilling muds are used extensively in ground drilling particularly for oil and gas exploration. The composition of the drilling mud is critical to particularly, though only, controlling the pressure conditions of the hole. For example, the composition of the drilling mud can be varied to provide an under pressure or overpressure condition as required in the hole; as well as to kill a well.

In order to ensure the correct drilling mud composition it is common for a specialist mud engineer to be on-site 24 hours a day to monitor downhole conditions and ensure the drilling mud composition is as required to achieve a desired effect. Due to the margins involved in oil and gas industry the cost of the specialist mud engineers can be readily absorbed and amortised. However, this is not the case for mineral exploration which may be typically conducted using a land-based mobile drill rig operating in regional/outback areas with two operators. While drilling mud is still critical for efficient mineral exploration drilling the risk of catastrophic events due to lack of control of downhole pressure conditions is substantially lower than for oil and gas exploration. For this and other reasons the cost of having a specialist mud engineer on-site 24 hours a day cannot usually be not justified for mineral exploration.

To address the lack of on-site drilling mud expertise it is a regular practice in the mineral exploration industry to provide the ingredients for the drilling mud and mixing instructions to the drill rig operators. There is an expectation that the drill rig operators will follow the instructions to provide a supply of drilling mud to meet predicted ground conditions. However, there is no substantive quality control and no ability to modify the drilling mud composition in the event that downhole conditions are not in line with predictions.

There is therefore a need in at least the mineral exploration industry for a system and method to facilitate the management of drilling mud.

Any discussion of the background art throughout this specification should in no way be considered as an admission that such background art is prior art, nor that such background art is widely known or forms part of the common general knowledge in the field in Australia or worldwide.

The above description of the background art is not intended to limit the application of the system and method as disclosed herein. In particular the disclosed method and system are not limited to application in the area of mineral exploration and may also be used for example in oil and gas exploration.

SUMMARY OF THE DISCLOSURE

In a first aspect there is disclosed an automated batch sampling drilling mud management system comprising:

a portable mud measurement system having: one or more measurement devices arranged to measure at least one property and/or characteristic of drilling mud; and a pumping system arranged to pump a batch sample of drilling mud from a supply of drilling mud to the one or more measurement devices and subsequently flush the batch sample of drilling mud from the one or more measurement devices; and a communications system enabling bidirectional communications between the mud management system and a remote location to enable transfer of data therebetween and the exertion of control from the remote location to the mud management system.

In one embodiment the automated drilling mud management comprises a dosing system arranged upon instruction from: the mud measurement system; or the communications system; to automatically dose the drilling mud supply with one or more drilling mud ingredients on a basis of minimising differences between the measured at least one property or characteristic of the mud and a desired specification.

In one embodiment the automated drilling mud management comprises an interface to enable a local operator to enter data relating to a manual additional of one or more ingredients to the drilling mud supply and wherein the communications system is arranged to communicate the entered data to the remote location.

In one embodiment the mud measurement system is arranged to automatically issue a notification at least one property or characteristic of the mud falls outside the desired specification.

In one embodiment the mud management system is arranged to provide feedback control in association with the dosing system and the mud measurement system to perform a test cycle on the mud after operation of the dosing system and cause subsequent operations of the dosing system and the mud management system where the measurement devices indicate that the characteristics or properties of dosed mud lie outside the desired specification.

In one embodiment the automated drilling mud management comprises a supply of one or more components or ingredients for making drilling mud operatively associated with the dosing system.

In one embodiment the dosing system includes an inventory control system arranged to receive data relating to the supply of the one or more components or ingredients to facilitate ordering of additional components or ingredients.

In one embodiment the automated drilling mud management comprises a supply of a flushing fluid for delivery by the pumping system to the one or more measurement devices.

In one embodiment the pumping system is arranged to circulate mud from an external mud supply through a hose and back to the mud supply through a return pipe prior to delivering a batch sample of mud to the one or more measurement devices.

In one embodiment the pumping system is arranged to maintain a volume of the flushing fluid in contact with the one or more measurement devices after a measurement cycle in which the one or more measurement devices have measured the at least one property or characteristic of drilling mud.

In one embodiment the pumping comprises a mud pump and a separate flushing fluid pump; wherein the pumping system is arranged to: run the flushing fluid pump to introduce a flushing fluid into the one or more measurement devices; and subsequently operate the mud pump to empty the flushing fluid from the one or more measurement devices.

In one embodiment the mud pump is reversible to enable the mud pump to pump the mud sample or the flushing fluid from the one or more measurement devices to the mud supply.

In one embodiment the pumping system comprises valve connected between the mud pump, the return pipe and the one or more measurement devices, the valve having: a recycling state where the valve directs mud from the pump to flow only to the return pipe; and a flow-through state where the valve allows mud to flow from the pump to the at least one more measurement devices and blocks flow of mud to the return pipe.

In one embodiment the automated drilling mud management comprises a single reversible pump having first and second ports and a first three-way valve connected between the first port, the supply of drilling mud and the one or more measurement devices; and a second three-way valve connected between the second port of the pump, the supply of drilling mud and the supply of flushing fluid.

In one embodiment the automated drilling mud management comprises a filtrate measurement system arranged to measure fluid loss of the drilling mud;

In one embodiment the automated drilling mud management comprises a mobile unit carrying the mud measurement system, and the communication system.

In one embodiment the mobile unit further carries one or more of: the dosing system; the supply of one or more components or ingredients for making drilling mud; the supply of flushing fluid; and the filtrate system.

In a second aspect there is disclosed a drilling mud management system comprising:
a portable housing;
one or more measurement devices are arranged to measure at least one property or characteristic of drilling mud, the one or more measurement devices being located within the housing;
a pumping system located within the housing and arranged to pump a sample of mud to the one or more measurement devices and subsequent pump the sample from the housing.

In a third aspect there is disclosed a drilling mud measurement system comprising: a portable housing;
one or more measurement devices that are arranged to measure at least one property or characteristic of drilling mud, the one or more measurement devices being located within the housing; and
a pumping system located within the housing and arranged to pump a sample of mud to the one or more measurement devices and subsequent pump the sample from the housing the pumping system having a mud pump and a separate flushing fluid pump;
wherein the pumping system is arranged to: run the flushing fluid pump to introduce a flushing fluid into the housing and the one or more measurement devices; and subsequently operate the mud pump to empty the flushing fluid from the one or more measurement devices.

In a fourth aspect there is disclosed an automated portable drilling mud measurement system comprising:
a portable housing containing:
one or more measurement devices arranged to measure at least one property and/or characteristic of drilling mud wherein one of the properties measured is viscosity; and
a pumping system located within the housing and arranged to pump a sample of mud to the one or more measurement devices and subsequent pump the sample from the housing, the pumping system arranged to pump a sample volume of drilling mud no more than 1 L to the one or more measurement devices.

In a fifth aspect there is disclosed an automated portable drilling mud measurement system comprising:
a portable housing containing:
one or more measurement devices arranged to measure at least one property and/or characteristic of drilling mud; and
a pumping system located within the housing, the pumping system arranged to pump a sample of drilling mud to the one or more measurement devices and subsequently flush the sample of drilling mud from the housing.

In some embodiments of some the above aspects the pumping system is arranged to maintain a volume of the flushing fluid in contact with the one or more measurement devices after a measurement cycle where the one or more measurement devices have measured the at least one property or characteristic of drilling mud.

In some embodiments of some the above aspects the mud pump is arranged to pump the sample of mud from an external mud supply through a hose to enable all of the properties and/or characteristics to be measured.

In embodiments of the above aspects the mud pump is reversible to enable the mud pump to pump the mud sample from the housing to the mud supply.

In one embodiment of the above aspects the pumping system comprises a return pipe capable of receiving mud from the mud pump pumped in a forward direction to enable a recirculating flow of mud from the supply through the hose and mud pump and back to the supply. In this embodiment the pumping system comprises valve connected between the mud pump, the return pipe and the one or more measurement devices, the valve having: a recycling state where the valve directs mud from the pump to flow only to the return pipe; and a flow-through state where the valve allows mud to flow from the pump to the at least one more measurement devices and blocks flow of mud to the return pipe. Also, in this embodiment the flush fluid pump may be arranged to introduce flushing fluid into the housing at a location downstream of where the return pipe receives mud from the mud pump operated in the forward direction, and upstream of the one or more measurement devices.

In one embodiment of the above aspects the pumping system may be arranged to operate in a flushing cycle in which the flushing fluid pump pumps flushing fluid into the housing and the drilling mud pump is operated in a reverse direction wherein the flushing fluid flows through the one or more measurement devices and the drilling mud pump and into the drilling mud supply.

In one embodiment of the above aspects the pumping system comprises one or more positive displacement pumps. The pumps may be peristaltic pumps.

In one embodiment of the above aspects at least one property or characteristics of the drilling mud comprises any one or more of:

Filtrate measurement
pH range 0-14
Chloride ion concentration in mg/L
Total Hardness determination in mg/L
Potassium ion concentration in mg/L
Calcium ion concentration in mg/L
Selective ion determination as required by the circumstances
Viscosity characteristics including
    Yield Point in lbs/100 ft$^2$
    Plastic Viscosity in Centipoise
    Marsh Funnel in seconds per quart/per litre
    Temperature in either ° C. or ° F.
    Rheology determined by the below parameters
        600 rpm
        300 rpm
        6 rpm
        3 rpm
        10 sec gel
        10 min gel
Density (SG)
Solids %
Solids removal efficiency In some embodiments the drilling mud measurement system comprises a mud density measurement system having at least two fluid pressure transducers the pressure transducers arranged to be suspended at a known vertical separation from each other in a volume of the drilling mud.

In one embodiment the drilling mud measurement system comprises a float arranged to suspend the at least two fluid pressure transducers above a bottom of a container or other receptacle or reservoir holding the volume of drilling mud.

In one embodiment the drilling mud measurement system is arranged to provide real time or near real-time information from the one or more measurement devices to an in-situ user of the drilling mud management system.

In one embodiment the drilling mud measurement system comprises an electronic data collection system arranged to automatically collect measurement data from the one or more measurement devices.

In one embodiment the drilling mud measurement system is arranged to make an in situ comparison between the measurement data and reference data relating to properties and/or characteristics of the drilling mud and provide, to a user of the drilling mud measurement system, information indicative of (a) the properties and/or characteristics of the drilling mud; and/or (b) one or more differences between the measurement data and reference data.

In one embodiment the drilling mud measurement system comprises one or both of (a) an internal memory device capable of storing the reference data; and (b) a provision for receiving the reference data from an external source.

In one embodiment the drilling mud measurement system comprises a data communication system arranged to electronically transmit the measurement data to a remote location.

In one embodiment data communication system constitutes the provision for receiving the reference data.

In one embodiment the provision for receiving reference data comprises a socket or connection for connecting with a portable external memory device.

In one embodiment the drilling mud measurement system is arranged for operable association with a dosing system wherein the dosing system is arranged upon instruction from the drilling measurement system to dose the drilling mud supply with one or more drilling mud ingredients on a basis of minimising differences between the measurement data and the reference data.

In one embodiment the drilling mud measurement system comprises an audit system arranged to automatically issue a notification when a quantity of a drilling mud ingredient in a supply of one or more drilling mud ingredients falls below a threshold level.

In one embodiment the drilling mud measurement system comprises a filtrate measurement system arranged to measure loss of a fluid component of the drilling mud.

In one embodiment the drilling mud measurement system comprises a dosing system arranged upon instruction from the drilling measurement system to dose a drilling mud supply with one or more drilling mud ingredients on a basis of minimising differences between the measured at least one property or characteristic and respective corresponding reference properties or characteristics.

In one embodiment the drilling mud measurement system comprises an electronic controller enabled to automatically control the one or more measurement devices and the pumping system.

In one embodiment the drilling mud measurement system comprises one or both of a local user interface and remote user interface for inputting instructions for execution by the controller to automatically control the one or more measurement devices and the pumping system In one embodiment the drilling mud measurement system comprises a power module arranged to connect with and provide power to one or more of the: one or more measurement devices; the pumping system; the filtrate measurement system;
and the dosing system.

In a seventh aspect there is disclosed method of measuring properties or characteristics of a drilling mud comprising:
    using a pump system in a housing to pump a mud sample into the housing;
    measuring at least one property or characteristic of the mud sample while in the housing; and
    using the pumping system to pump the mud sample from the housing.

DESCRIPTION OF THE DRAWINGS

Notwithstanding any other forms which may fall within the system and method as set forth in the Summary, specific embodiments will now be described, by way of example only, with reference to the covering drawings in which.

DETAILED DESCRIPTION OF SPECIFIC EMBODIMENTS

Figure 1:
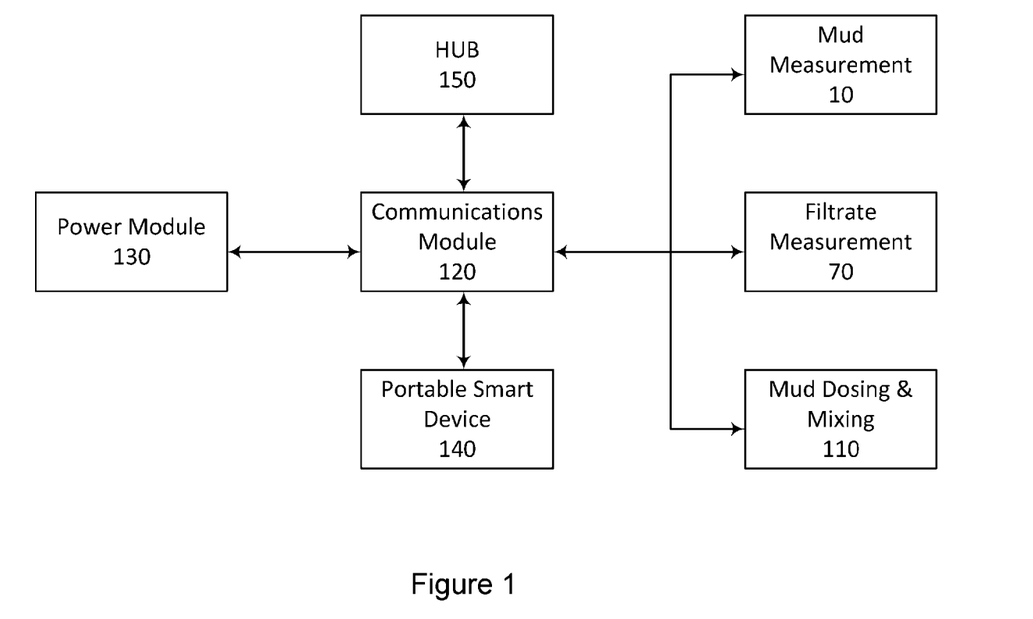
FIG. 1 is a schematic representation of an embodiment of the disclosed drilling mud management system and which may be used to perform the disclosed method.

FIG. 1 is a schematic layout of an embodiment of the disclosed drilling mud management system 1 (hereinafter referred to as the "system 1"). The system 1 includes at least a mud measurement system 10 which is arranged to measure at least one property and/or characteristic of the drilling mud (also known as "drilling fluid"). Additional subsystems or modules of the system 1 include: a filtrate measurement system 70; a mud dosing and mixing system 110; a communications module 120; a power module 130; and a portable "smart" device 140. Each of the modules and subsystems 10, 70, 110, 120, 130 and 140 is a stand-alone item with plug and play connectivity to provide corresponding functionality to the system 1. The hub 150 shown in FIG. 1 is not a part of the system 1, but rather is a remote data collection and storage facility with which the system, 1 is able to communication. The hub 150 may be a cloud-based system.

As explained in the following description the system 1 provides a portable and in substance complete and automated mud management system for drilling without the need for an on-site mud engineer. The management provided by the system 1 includes measurement and diagnostics of the mud, the ability to automatically vary the mud composition, conduct audits of mud characteristics compared with ratios of components used in mixing the mud, and just-in-time ordering and delivery of mud components to site. The mud management system 1 is automated to the extent that once it has been set up it is able to function automatically to perform a measurement of the characteristics of the mud, the filtrate, and operator otherwise control the mud dosing and mixing system 110. The system can be activated to perform its automates functions either locally by for example a drill operator, or remotely using the communications system.

Each of the individual modules and subsystems 10, 70, 110, 120, 130 and 140 will now be described.

Mud Measurement System 10

Figure 2A:
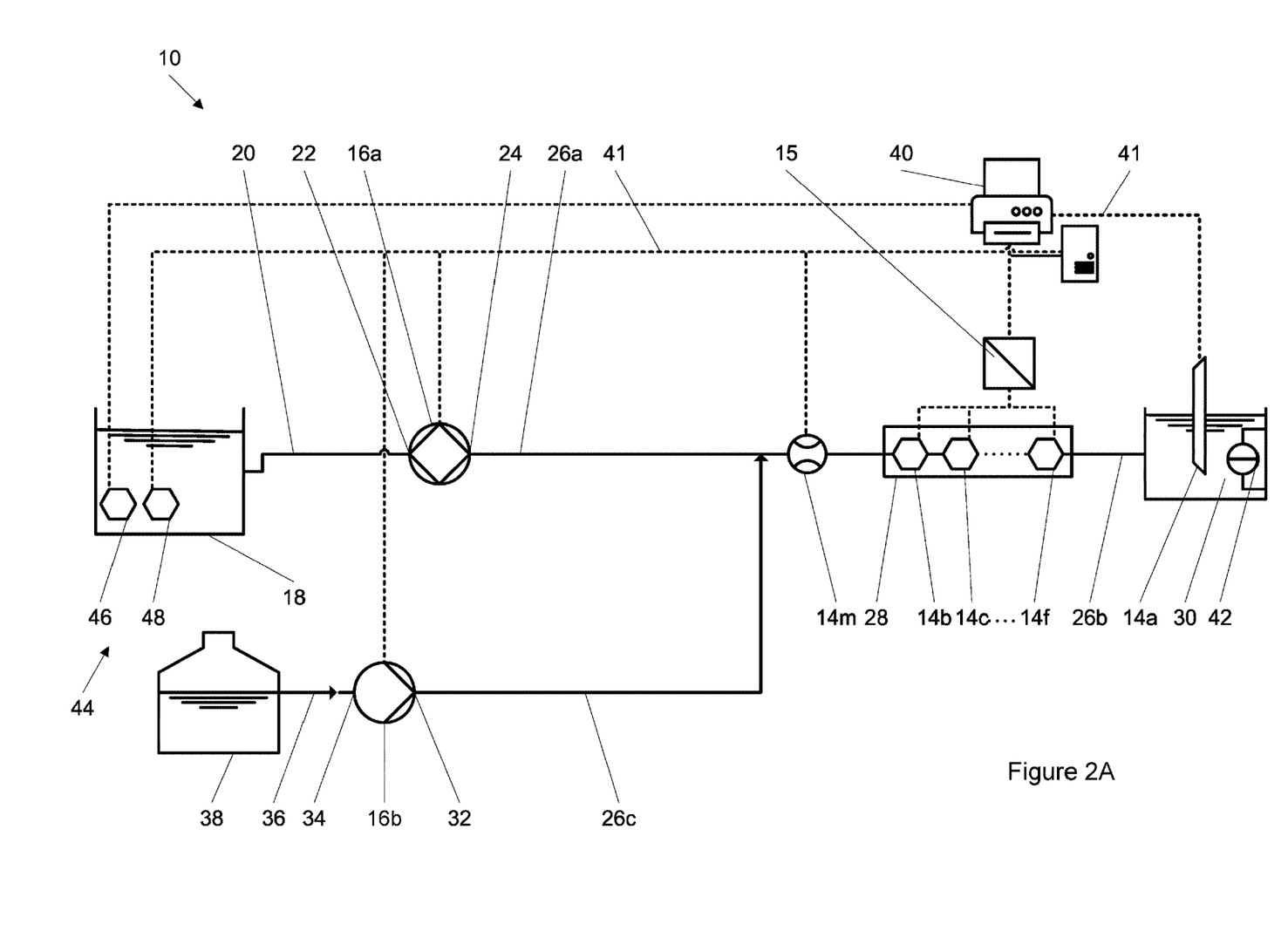
FIG. 2A is a schematic representation of a drill mud measurement system which may constitute or form part of a first embodiment of the drilling mud management system shown in FIG. 1.

FIG. 2A shows a schematic representation of mud measurement system 10 (hereinafter referred to in general as "system 10") which includes a housing 12 (illustrated in FIG. 3) that houses measurement devices 14a-14f (hereinafter referred to in general as "measurement devices 14") and a pumping system 16. The measurement devices 14 are arranged to measure at least one property or characteristic of drilling mud. The pumping system 16 is arranged to pump a batch sample of mud to one or more of the measurement devices 14 and to subsequently pump the mud sample from the one or more of the measurement devices 14 and housing 12. By conducting batch sampling, a static sample of mud is presented to the measurement devices 14. The system 10 is a low-pressure system, with the only pressure applied to the sample when being delivered to the measuring devices being the that provided by the pumping system which utilities one or more low pressure positive displacement pumps.

As the pumping system 16 is within the housing it relies on applying a suction or relative negative pressure to draw mud and other fluids into the housing 12 and the measurement devices 14. As also explained below the pumping system 16 is operable in a reverse direction to pump out or otherwise flush fluids from the housing 12.

The pumping system 16 includes a drilling mud pump 16a and a flushing fluid pump 16b. The pumps 16a and 16b are separately controlled. In this embodiment the pumps 16a and 16b are positive displacement pumps such as, but not limited to, peristaltic pumps. Peristaltic pumps are inherently low-pressure pumps. The pumping system 16a is connected to an external supply 18 of drilling fluid via a hose 20. The hose 20 is connected to one port 22 of the drilling mud pump 16a. A second port 24 of the drilling mud pump 16a is connected by a conduit 26a to a manifold 28. The manifold 28 is connected by a conduit 26b to a cup 30. A conduit 26c connects a port 32 of the flushing fluid pump 16b to the conduit 26a. A second port 34 of the flushing fluid pump 16b is in fluid communication via a hose 36 with a supply 38 of freshwater or other flushing fluid.

One of the measurement devices 14a measures characteristics of fluid contained within the cup 30. In this embodiment the measurement device 14a is a viscometer or rheometer. A plurality of the measurement devices 14b-14f is arranged to measure other characteristics or properties of fluid in the manifold 28.

In one embodiment the viscometer/rheometer 14a can be arranged to provide the following measurements and tests on the fluid contained within the cup 30:

Yield Point
Plastic Viscosity
Temperature
10 Sec Gel
10 min Gel
Viscosity
600 r.p.m
300 r.p.m
6 rpm
3 rpm In this particular embodiment the measurement devices 14b-14f may comprise respective probes to measure characteristics/properties of the fluid in the manifold 28 such as but not limited to:

14b: pH
14c: chloride ion combination
14d: total hardness
14e: potassium ion combination
14f: calcium ion combination The number and type of probes that are provided can vary from application to applications and thus can be more, less and/or different probes to the five mentioned above.

The above list of characteristics may be augmented by the inclusion of a filtrate measurement system in the housing 12. This is described in greater detail later under the heading "Filtrate Measurement System 70".

In one possible example the probes 14b-14f may be in the form of an ion-selective electrodes (ISE), also known as a specific ion electrodes (SIE), which are transducers (or sensors) that convert the activity of a specific ion dissolved in a solution into an electrical potential (i.e. voltage). The voltage is dependent on the logarithm of the ionic activity, according to the Nernst equation. The electrical potential is measured in Bi-polar millivolts. This potential is connected to respective converters 15b-15k (hereinafter referred to in general as "converters 15") which in turn converts the millivolt signal to a 0-20 milliamp analogue signal.

The system 10 also includes an electronic controller 40 located within the housing 12. Conveniently the controller 40 may be in the form of a programmable logic controller. A user interface (not shown) including for example a display and one or more buttons (touch screen or physical) is provided to enable a user to operate the controller 40 and thus the system 10. A local communications network represented by dashed lines 41 provides a communication and control path for the controller 40 to other components of the system 10. The local network may comprise wires, optical cables, wireless devices, or any combination thereof.

The controller 40 is connected to the measurement devices 14 via the corresponding converters 15 and the pumping system 16. Additionally, the controller 40 is connected to fluid level system that is used to provide information relating to the level of fluid within the cup 30; and, a mud density measurement system 44.

The fluid level system in this embodiment is in the form of a flowmeter 14*m* which is downstream of the pumping system 16 and upstream of the cup 30 with reference to a direction of flow of mud from the supply 18 or 38 to the cup 30. In this embodiment the flowmeter 30 is between the pumping system 16 and the manifold 28. The flowmeter 14*m* measures the flow of liquid into and out from the cup 30. This measurement is used by the controller 40 to determine the level of liquid in the cup 30.

The fluid level system may additionally or alternately comprise a level sensor 42 which is arranged to provide a reading of the level of fluid within the cup 32 the controller 40. When used in addition to the flowmeter 14*m*, the level sensor 42 provides a degree of redundancy and self-checking. The level sensor 42 optical sensor can be located on an outside of the cup 30. In this event the cup 30 is made from a transparent material such as glass or polycarbonate. However other types of level sensors may be used such as electrical conduction sensors or ultrasonic sensors. Alternately the level sensor 42 can be in the form of a float located inside of the cup 30.

The mud density measurement system 44 comprises at least two hydrostatic pressure transducers 46 and 48 (hereinafter "transducers 46 and 48"). The mud density measurement system 44 may be held within a storage compartment of the housing 12. However, when the system 10 is in use measuring characteristics or properties of the drilling fluid/mud the mud density, the measurement system 44 is removed from the housing 12 and placed into the external supply 18 of drilling fluid.

The transducers 46 and 48 are held or otherwise suspended at different respective heights or depths within the external supply 18 of drilling fluid/mud. In one example the transducers 46 and 48 may be submerged in the supply 18 in the range of 200 mm to 2000 mm. Any vertical separation or offset between the transducers 46 and 48, which will provide a basis for calculating mud weight. Nevertheless, accuracy of the mud weight calculation may be enhanced by maximising the vertical separation. In one example this separation may be a minimum of 100 mm.

Due to the difference in respective depths within the external supply 18 the transducers 46 and 48 are subjected to different fluid pressures. This difference in pressure is directly dependent upon the respective volumes of drilling fluid bearing on the transducers 46 and 48. Given that the difference in level between the sensors 46 and 48 is known or can be set by an operator, and the configuration of a container or other receptacle forming the supply 18 is known, the controller 40 can be programmed to automatically calculate the density of the drilling fluid using the differences in fluid pressure sensed by the sensors 46 and 48.

The mud density measurement system 44 can be placed at any depth or location within the external supply 18. Accordingly, embodiments of the present system 10 enable the mud density measurement system 44 to be spaced above the bottom of the external supply 18. This can be achieved for example by using a float which is attached to both of the sensors 46 and 48. By suspending the measurement system 44 above a bottom of the external supply 18 it is possible to minimise measurement errors which may otherwise arise due to the settling of solid particles within and near the bottom of the external supply 18.

Electrical power to operate the system 10 can be provided by way of the power module 130. Alternately or additionally the system 10 may include batteries (rechargeable or otherwise) to provide power or backup power. If rechargeable batteries are provided, and the power module 130 is not available, optionally an external solar electric panel can be provided to facilitate recharging of the batteries.

An exemplary operating cycle of the system 10 will now be described.

The system 10 in the housing 12 is transported to a drilling location where drilling mud is to be used. It is envisaged that the housing 12 may be of the general size and figuration of a piece of luggage suitable for carrying as checked in luggage on a commercial aircraft. To this end the housing 12 can be provided with a retractable handle and wheels (neither being shown). Alternately the mud management system 1 incorporating: the mud measurement system 10, inclusive of its housing 12; and one or more of the filtrate measurement system 70; mud dosing and mixing system 110; communications module 120; and power module 130; is transported to the drilling location, for example in a trailer or on a powered vehicle.

Once on-site the mud density measurement system 44 is taken out of the housing 12 and placed within the external supply 18 ensuring that the transducers 46 and 48 are free to be suspended at a known vertical/depth offset from each other. The external supply may for example be inside of a hole being drilled in the ground. A free end of the hose to 20 (i.e. the end not coupled to the port 22) is placed in the external supply 18. Likewise, a free end of the hose 36 (i.e. the end not coupled to the port 34) is placed in the freshwater supply 38. The mud management system 1 and/or the mud measurement system 10 can be activated locally by the drill rig operator and then function automatically, or remotely using the communications system 120 by a mud engineer or other officer; or a combination of both where for example a mud engineer may sent instructions for communication system 120 to the drill rig operator to perform various functions.

The controller 40 may be ideally, but not necessarily, provided with a set of reference parameters pertaining to the drilling mud. These parameters for example may be desired characteristics of the drilling mud to be used in a particular drilling application. In the event the controller 40 is not preloaded with the reference parameters, they may be provided by the remote mud engineer via the communication system 120.

The controller 40 is switched to a measurement cycle mode. This mode executes two cycles, a fill cycle in which the cup 30 and manifold 28 are filled with drilling fluid, and a data cycle where the sensors 14*a*-14*f* are activated to provide measured data relating to the drilling fluid. In the fill cycle of this mode the controller 40 operates the drilling fluid pump 16*a* to draw drilling fluid into the housing 12. Thus, the port 22 acts as an inlet port and the port 24 acts as an outlet port. The drilling mud is passed by the conduit 26*a*, through the flowmeter 14*m* to the manifold 28 and by the conduit 26*b* to the cup 30. This transfer of drilling fluid continues until the controller 40 using measurements from the flowmeter 14*m* senses that the drilling fluid within the cup 30 has reached a prescribed level. It is envisaged that the total volume of drilling fluid/mud pump into the housing 12 to facilitate measurement of the desired characteristics and properties will be in the order of between 0.3 L to 1 L. In one example of the volume required to carry out all of the tests and measurements may be in the order of 0.7 L.

The controller 40 now ceases the fill cycle by stopping the pump 16a and the data cycle starts where the controller 40 operates or otherwise polls the sensor 14 for data relating to specific characteristics or properties of the drilling fluid. In this particular embodiment the controller 40 will operate the viscometer 14a to conduct the measurements and tests described above, and subsequently received corresponding measurement data. Similarly, the controller 40 receives measurement data regarding the characteristics or properties measured by the sensors 14b-14f.

From a display on the controller 40 a drill rig operator can view the characteristics or properties of the drilling fluid and compare them to the prescribed or desired characteristics. The prescribed or desired characteristics may be provided to the driller in a variety of different ways. For example, by way of a written document in a mud preparation/handling manual. Alternately these characteristics may be provided in an electronic memory of the controller 40 (e.g. pre-programmed in the controller 40); a portable memory device connectable to or otherwise able to communicate with the controller 40; or by download into an electronic memory of the controller 40 from a remote location via a remote user interface.

Irrespective of how the prescribed mud characteristics are conveyed to the operator, the operator is informed by the controller 40 of the measured mud characteristics. From here either (a) the operator can determine the differences if any between the measured and prescribed characteristics of the drilling mud, or (b) the controller 40 can determine and inform the operator of the differences if any between the measured and prescribed characteristics of the drilling mud. Once the differences are known, the operator (or, as described later, the system 110 if in use in the system 1) is able to take corrective action to vary the composition of the drilling mud to minimise or reduced to zero these differences.

Once the measurement cycle has been completed the controller 40 can be switched to a flushing cycle mode. In this mode the controller 40 controls the drilling fluid pump 16a to operate in a reverse direction so as to pump the drilling fluid out of the housing 10. Therefore, in the flushing cycle the port 24 is an inlet port and the port 22 is an outlet port. After the pump 16a has pumped out the drilling mud; or simultaneously with the pump 16a being operated to pump out the drilling mud; the controller 40 operates the flushing fluid pump 16b to pump freshwater into the housing 12. The flushing fluid is a liquid such as but not limited to water. Specifically, the pump 16b pumps water from the external supply 38 via the hose 36 and through conduits 26c and conduit 26a filling the manifold 28 and the cup 30 until the controller 40, using measurements from the flowmeter 14m determines that cup 30 is full. The controller then stops the pump 16b and activates the viscometer 14a to spin at 600 rpm for a period of time. After this time period the viscometer 14a is stopped by controller 40 and subsequently the pump 16a is run in reverse. Port 24 is now a suction port and port 22 is a delivery or discharge port. The fluid in the cup 30 and manifold 28 is emptied via conduit 20 into external supply 18. This cleaning/flushing cycle may be repeated a number of times, such as but not limited to 2-4 times. After the last of the repeated cleaning cycles the pump 16b fills manifold 28 and cup 30 and stops. This is done so that the probes 14b-14f remain in a fluid whilst not being operated. The system 10 remains in this state up until a new measurement cycle starts. A new measurement cycle is started by running pump 16a in reverse to empty cup 30 and manifold 28 into external supply 18 via conduit 20.

The system 10 can be programmed to automatically conduct the measurement cycle and flushing cycles at regular intervals for example, but not limited to, every six hours, 12 hours or 24 hours.

Figure 2B:
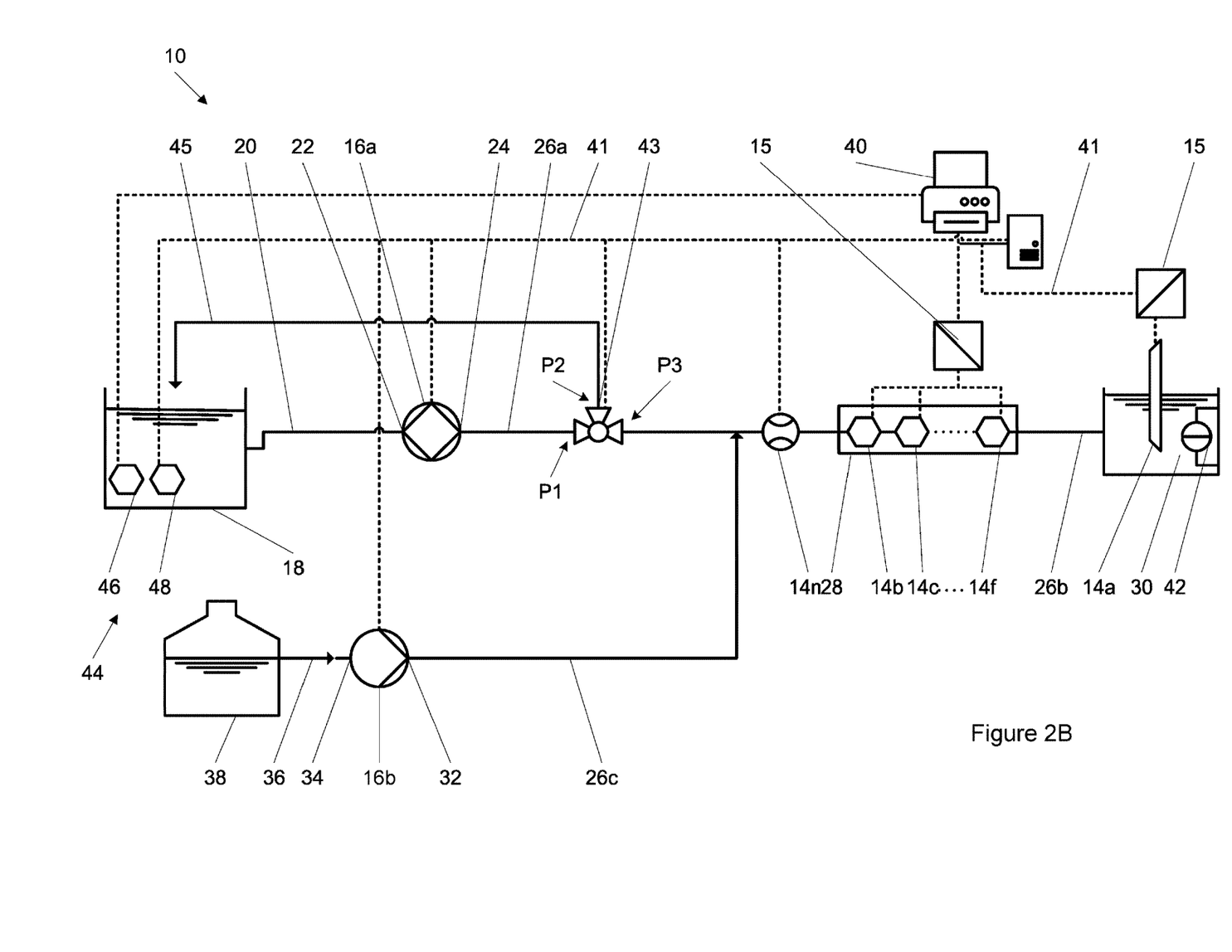
FIG. 2B is a schematic representation of a drill mud measurement system which may constitute or form part of a second embodiment of the drilling mud management system shown in FIG. 1.

FIG. 2B shows a second embodiment of the system 10. In the description of this embodiment the same reference numbers are used to denote the same features as in the first embodiment shown in FIG. 2A.

The system 10 shown in FIG. 2B is an enhancement of that shown in FIG. 2A and differs in terms of its structure and configuration only by the addition of a three-way valve 43 and a return pipe 45. The three-way valve 43 is connected into the conduit 26a via its ports P1 and P3; and the return pipe 45 is connected to a port P2 of the three-way valve 45 and the supply 18. The valve 43 is in communication with the via the local communications network 41.

The purpose of the return pipe 45 and three-way valve 43 is to modify the above described filling cycle to include a priming cycle in which drilling fluid is recirculated through the hose 20, valve 43 pipe 45 act to the supply 18. This minimises the risk of the drilling fluid being diluted prior to flowing into the cup 30 and manifold 28 due to the presence of water in the hose 20 remaining from a previous cleaning/flushing cycle. The recirculation is achieved by opening ports P1 and P2; and closing P3 on the valve 43, placing the valve in a recycling state; while running the pump 16a in the forward direction.

The duration of the priming cycle is dependent on the flow rate (i.e. the viscosity) of the drilling fluid and the length of the pipe 20. After this period of time the controller 40 closes the port P2 and opens the port P3 (the port P1 remaining open) allowing the drilling fluid to now flow through the flowmeter 14m, manifold 28 and into the cup 30. Here the valve 43 is in a flow through state. The controller 40 turns off the pump 16a when it determines that the cup 30 is filled to the predetermined level. This completes the fill cycle.

The controller 40 can now perform a measurement cycle taking readings from the viscometer 14a, and other senses 14b-14f. If desired, a second or indeed further measurement cycles can be performed without an intervening cleaning cycle. In this way multiple samples measurements can be made and averaged to minimise distortion of readings. To take multiple sample measurements, the controller 40 can be programmed to, after each measurement cycle, reverse the direction of the pump 16a to pump fluid from the cup 30 and delivered back to the supply 18. The pump is stopped, and the above cycle is restarted with the port P2 being opened, port P3 being closed and the pump 16a operated in the forward direction to recirculate the fluid through the pipe 45 back to the supply 18 for a predetermined period of time, after which the port P2 is closed and the port P3 opened to again fill the cup 30. Now the second or any subsequent sample measurement can be taken and averaged with a measurement of the previous sample in the same sample set.

After the sample measurements(s) have been taken the controller is switched to a flushing cycle mode which operates to empty the drilling fluid from the housing and subsequently clean the cup 30 and senses 14a-14f. While this is the same function as the flushing cycle mode described in relation to the first embodiment the specific method of operation is different. The steps are as follows:

a) the pump 16*a* is operated in a reverse direction with the ports P1 and P3 open and port P2 closed so that fluid in the cup 30 and manifold 28 is drained back into the supply 18, and the pump 16*a* is stopped (this is in substance the same as in the first embodiment);

b) the port P3 on the valve 43 is closed and the pump 16*b* is run to provide cleaning fluid such as water through the flowmeter 14*m* to fill the manifold 28 and cup 30;

c) when the cup 30 is detected as being filled the viscometer 14*a* is operated to spin for a period of time;

d) after that period of time the pump 16*b* is stopped, the ports P1 and P3 on the valve 43 are opened, the port P2 is closed, and the pump 16*a* is run in the reverse direction to drain the cleaning fluid from the cup 30 and manifold 28. Thus, the mud pump 16*a* is also flushed in this step.

The above steps a) through to d) may be repeated one or more times to enhance the degree of cleaning. Irrespective of how many times the steps a) through to d) are cycled, as a final step the port P3 can be closed and the pump 16*b* run to fill the manifold 28 and cup 30 with clean water or other flushing fluid so that the sensors 14*a*-14*f* remain wet prior to the next measurement cycle.

The embodiment of the mud measurement system 10 shown in FIG. 2B has the same measurement devices 14*a*-14*f* and is able to perform exactly the same measurements and determine the same characteristics of drilling mud, as the system 10 shown in FIG. 2A.

Figure 2C:
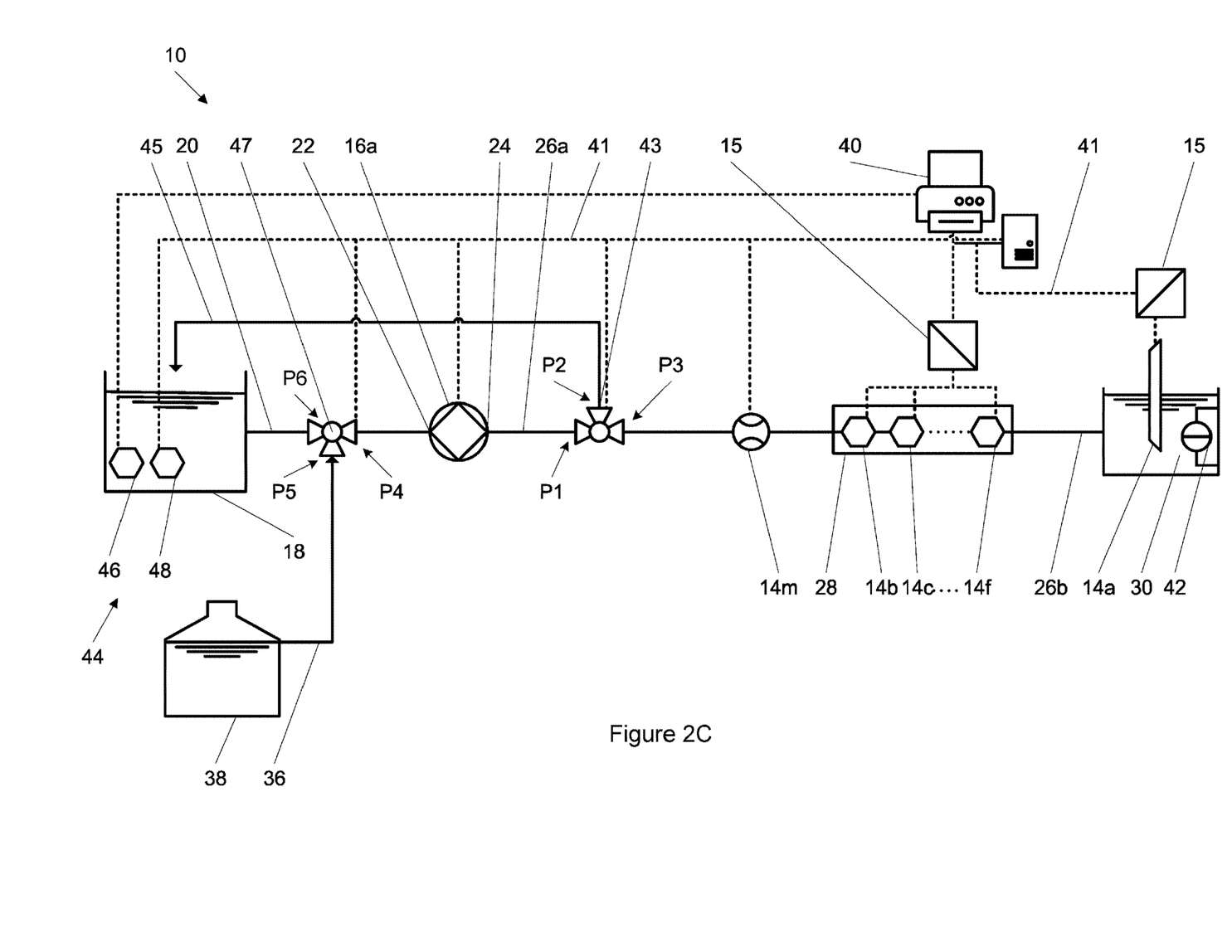
FIG. 2C is a schematic representation of a drill mud measurement system which may constitute or form part of a third embodiment of the disclosed drilling mud management system shown in FIG. 1.

FIG. 2C shows a second embodiment of the system 10. In the description of this embodiment the same reference numbers are used to denote the same features as in the second embodiment shown in FIG. 2B. For convenience the measurement devices 14 are not shown but are provided in the same manner as described above in relation to the embodiments in FIGS. 2A and 2B.

The substantive difference between the second embodiment shown in FIG. 2B and the third embodiment shown in FIG. 2C is the replacement of the flushing fluid pump 16*b* a second three-way valve 47. The valve 47 is in the conduit 20 between the mud supply 18 and the port 22 of the pump 16*a*. The valve 47 has a port P4 in communication via a conduit 20*a* to the port 22 of the pump 16*a*. Thou 47 also has a port five which communicates with the flushing fluid supply 38 for the conduit 36; and a port P6 the communicates with the drilling mud supply 18 via the conduit 20.

The operation/fluid flow in the embodiment of the system shown in FIG. 2C is as follows.

To condition or prime the system to provide a representative batch sample of mud to the manifold 28 and cup 30, in the valve 43 the ports P1 and P2 are open and the port P3 is shut, while in valve 47 ports P4 and P6 are open and port P4 is shut. The pump 16*a* can now be operated in any direction which will cause a circulating flow of mud through the conduit 20, valve 47, pump 16*a*, valve 43, conduit 45 and the supply 18.

To present a batch sample of mud from the supply 18 to the devices in the manifold 28 and cup 30 ports P1 and P3 of thou 43 are opened while the port P2 is shut, and the ports P4 and P6 of thou 47 open while the port P5 is shut. The pump is now run in a direction so that the port 22 is the suction or inlet port and the port 24 is the outlet port. This draws a sample of mud from the supply 18 through the conduit 20, valve 47, through the pump 16*a*, the valve 43 and the flowmeter 14*m* to the probe manifold 28 and the cup 30.

In order to flush or clean the manifold 28 and cup 30 the port P2 on the valve 43 is shut, the ports P1 and P2 are open; ports P4 P5 of thou 47 open while port P6 is shut and the pump 16*a* is operated in the same direction as before with the port 22 being the suction or inlet port and the port 24 the outlet port. Now cleaning fluid is drawn through the conduit 36 to the valve 47, pump 16*a*, valve 43, flowmeter 14*m* and to the manifold 28 and cup 30. The pump stops when the flowmeter 14*m* indicates that the cup 30 is filled to a predetermined level. The viscometer associated with the cup 30 can be operated at this time for cleaning purposes. The cleaning fluid can be now flushed or removed from the system by closing port P5, opening port P6 and then operating the pump 16*a* in a reverse direction so that port 24 becomes a suction port and port 22 the outlet port. The cleaning fluid is then expelled through the flowmeter 14*m*, the valve 43, the pump 16*a* and the valve 47 through the conduit 20 to the supply 18.

A communications facility enables the system 10 to transmit the measured mud properties and characteristics to a remote location, as well as to receive information including but not limited to prescribed mud present characteristics. The communications facility may be provided as an integral part of the system 10 and housed within the housing 12. Alternately the separate communications module 120 shown in FIG. 1 can be connected to the system 10 to provide the same communications functionality.

Figure 3:
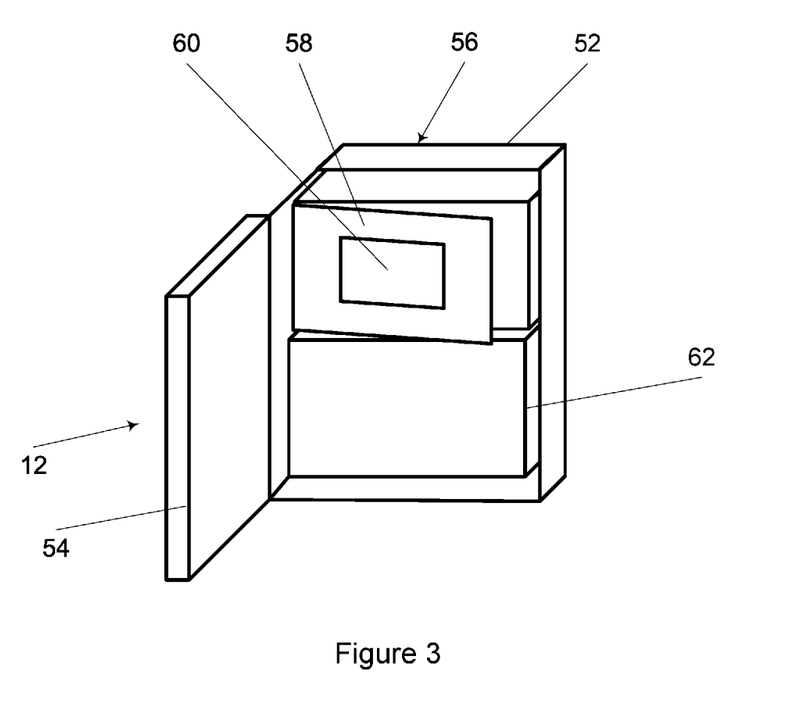
FIG. 3 is a schematic representation of a housing for the drill mud measurement system shown in FIG. 2A or FIG. 2B.

The communication functionality whether provided as part of the system 10 or in the module 120 may be used to monitor the mud quality or appropriateness for the conditions at hand and enable feedback via a remote operator to the drill rig operators. Additionally, the information can be used for audit or inventory control purposes including for example to automatically arrange transport of additional supplies of mud ingredients if it is determined that the supply FIG. 3 shows the housing 12 as a case having a main compartment 52 and a hinged lid 54. Inside the case is an upper sub compartment 56 having a door 58. The controller 40 is in the upper sub compartment 56 with its display visible and user interface accessible thought an opening 60 in the door 58. A lower sub compartment 62 houses the measurement devices 14 and the pump system 16. A door (not shown) on the lower sub compartment 52 provides access to devices 14 and pump system 16. Space within the main compartment 52 and outside of the sub-compartments 56 and 62 can be occupied by the mud density measurement system 44 on the hoses 20 and 36.

Filtrate Measurement System 70

Figure 4:
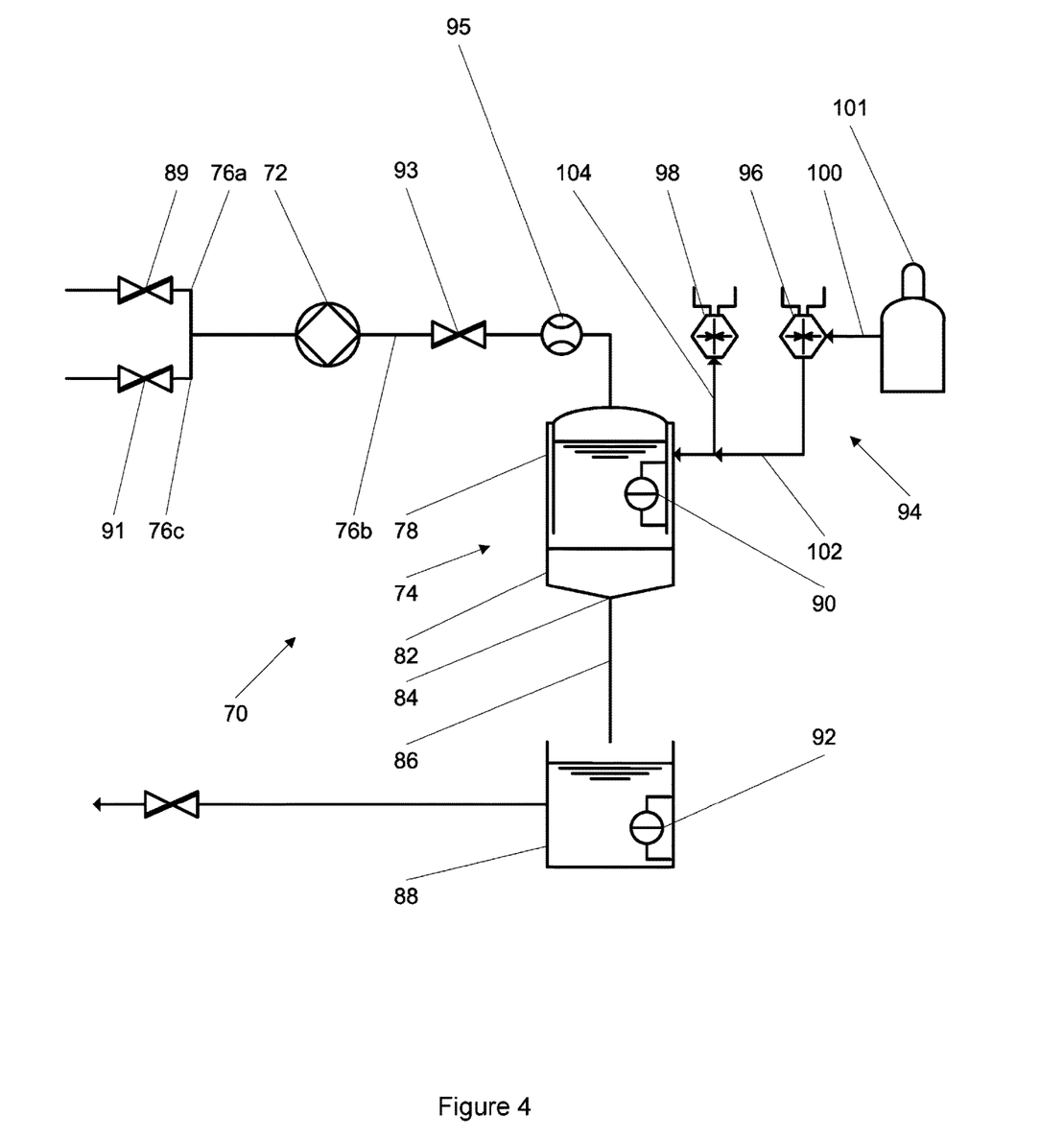
FIG. 4 schematic representation of a filtrate management system which may be incorporated in either the drilling mud management system shown in FIG. 1 or the drill mud measurement system shown in either FIG. 2A or FIG. 2B.

FIG. 4 is a schematic representation of the filtrate measurement system 70. The filtrate system 70 is operatively associated with the system 1. The operative association can be by way of the system 70 being:

a part of the system 10 and contained within the housing 12 and controlled by the controller 40 (in that event "filtrate measurement" would be an additional characteristic that could be measured and placed on the list of other characteristics measured by the devices 14 on page 5 above);

a modular part of the system 10 where it is in its own housing but contained within the housing 12 and controlled by the controller 40 separate to the system 10 and contained with its own housing but connectable to system 10 (and thus the controller 40), the communications module 120, power module 130, portable smart device 140, and the hub 150, as shown in FIG. 1.

The filtrate measurement system 70 comprises a pump 72 to enable the pumping of a volume of the drilling fluid into a measurement cell 74 via conduits 76*a* and 76*b*. The measurement cell 74 is formed with a cylindrical container 78. A base 82 of the measurement cell 74 has an opening covered by a filtering device such as a mesh screen or filter paper (not shown) leading to an outlet 84. The outlet 84 feeds, via a conduit 86, filtrate to a collection and measurement vessel 88. A level sensor 90 senses the volume of mud within the measurement cell 74. The level sensor 92 measures the level or volume of filtrate collected in the vessel 88.

An arrangement of the solenoid valves 89, 91 and 93 is associated with the pump 72 and the cell 74. The solenoid valve 89 is controllable to open and close the fluid conduit 76*a* that provides fluid communication between a sample of mud and the pump 72. The solenoid valve 91 is controllable to open and close a conduit 76*c* that provides fluid communication between a supply of a cleaning or flushing fluid and the pump 72. The solenoid 93 is controllable to open and close the conduit 76*b* enabling fluid pumped from the outlet of pump 72 to flow into the cell 74. A flowmeter 95 is in line between the valve 93 and the cell 74 to measure the volume of fluid flowing into the cell 74. The flowmeter 95 can be used in conjunction with the sensor 90 to enable determination of the volume of fluid within the cell 74. In one embodiment the flowmeter 95 can provide the primary indication of level with the sensor 90 used for redundancy or verification.

The filtrate measurement system 70 also includes a pressure system 94 which is arranged to apply pressure to the top of the container 78 thereby causing the fluid component of the mud within the cell 74 to flow through the filtering device, the outlet 84 and the conduit 86 into the vessel 88. Pressure system 94 comprises a pressurising solenoid 96, a pressure relief solenoid 98 and compressed gas conduits 100, 102, and 104. The conduit 100 is in fluid communication with a supply of compressed gas 101 such as, but not limited to, air, nitrogen or carbon dioxide. Flow of the compressed gas to the conduit 102, and subsequently to the cell 74 is controlled by the pressurising solenoid 96. The pressure of the compressed gas can be selectively relieved by operation of the pressure relief solenoid 98 which is in fluid communication with the conduit 102 via a conduit 104.

To begin a measurement of the filtrate the valves 89 and 93 opened, valve 91 is closed and the pump 72 is run to pump mud into the cell 74. When the level of mud reaches a prescribed level the sensor 90 sends a signal to the controller 40 which in turn turns off the pump 72. To provide filtrate measurements the valve 93 is closed and the pressurising system 94 is now operated. The solenoid 96 is opened and the solenoid 98 is closed. Pressurised gas flows through the conduit 100 and conduit 102 to apply pressure to the mud within the cell 74 which is forced through the filtering device and flows through the conduits 84 and 86 into the vessel 88. The filtering device will have a particular mesh or pore size to prevent the passage of oversized particles. The level sensor 92 determines the volume of filtrate collected in the vessel 88. This is used as an indication of the rate of volume loss of the fluid component of the mud, i.e. a measure of the amount of fluid loss in a borehole. Mudcake built up on the filter device can also be collected for analysis for various properties such as thickness, toughness, slickness and permeability.

After measuring the volume of filtrate, the cell 74 is depressurised. This involves closing the solenoid 96 to shut off fluid communication between a supply of compressed gas and the cell 74; and opening the pressure relief solenoid 98. Opening the solenoid 98 vents the compressed gas above the piston 82 to atmosphere. A cleaning cycle is now performed in which the cell 74 is filled with clean water and cleaned using an ultrasonic probe. This is achieved by closing the valve 89, opening the valves 91 and 93 and operating the pump 72 to pump fluid into the cell 74. The contents of the cell 74 is then dumped and the filtrate measurement system 70 is now ready for reuse. The filtrate in the vessel 88 can be subsequently emptied via a conduit 103 and valve 105.

Mud Dosing and Mixing System 110

The automated mud dosing and mixing system 110 communicates with respective supplies (not shown) of different components of the drilling mud. The supplies feed the components of the mud by respective chutes to a mixing vessel (not shown). The system 110 is also in communication with the systems 10 and 70. The systems 10 and 70 provide information to the controller 40 regarding the characteristics and properties of the mud. If the controller 40 or a mud engineer at a remote location which receives data from the system 10 decides that the mud is not to specification the system 110 can be commanded to change the composition of the mud for example by increasing or otherwise changing the concentration of one or more components/chemicals in the mud with a view to bringing the mud within specification.

When the controller 40 is preloaded with the mud specifications and the measurements indicate that the mud is outside of the specifications the controller 40 is able to automatically control the dosing system to bring the mud back within specification. However, if the controller 40 is not preloaded with the mud specifications or there is a perceived need to change the mud specifications, a mud engineer or other operator at a remote location can provide appropriate commands by the communication system 120 either via the controller 40 or directly to the mud dosing and mixing system 110 to vary the concentration of, or otherwise add, one or more of the mud components. In yet a further variation a database or artificial intelligence system is provided at the remote location with sufficient information and/or intelligence and processing capability to provide the mud specifications to the drilling location via the communication system 120.

In addition to the automated dosing described above manual dosing is also contemplated to allow a local operator, either using their own knowledge for troubleshooting, or at the direction of a remote mud engineer, to vary the mud composition by manually adding a component or ingredient that is not already available through the supply of components and ingredients. In this circumstance mud management system 1 is provided with an interface, for example through a keypad coupled to the controller 40, to enable a local operator to enter data relating to the newly added component or ingredient. In this way the information pertaining to the mud composition is always maintained. This data will be communicated automatically by the communication system 120 a remote location.

After the dosing system is being operated either automatically or manually the mud measurement system 10 can be run through a test cycle to conduct measurements of the characteristics and properties of the dosed mud to verify that it falls within the desired specification. This test cycle is identical to a normal measurement cycle. However, the mud management system 10 may be programmed to provide feedback control to automatically activate the dosing system to add further components or ingredients to the mud where the results of the test cycle show that the mud is outside of specification. The feedback control well automatically operated to dose and test the mud until the mud within the desired specification.

The drilling mud management system 1 may also include an inventory control system which keeps a record of use of the mud ingredients by the dosing system and sends a message via the communications system 120 to a remote location for ordering and delivering the mud components/chemicals to the drilling location. The ordering can be performed automatically by the communications system 120 sending instructions to a supplier or by a mud engineer or other operator who receives the message via the communications system 120 and then orders the required mud components/chemicals for delivery to the drilling location. The inventory control system may be a part of the dosing system or a standalone system. When the inventory control system is a stand-alone system it may be at the remote location and realised as a software application which receives data from the communication system 120 relating to the use of the mud components by the dosing system.

Communications Module 120

The communications module 120 provides one or more communications facilities to enable bidirectional flow of data, information, and messaging between a drill rig operator and one or more remote locations; as well as to enable a mud engineer or other operator to exert remote control over one or more of the mud measurement system 10, the filtrate measurement system 70, and the mud dosing and mixing system 110. This therefore enables remote mud management using locally measured mud characteristics and properties. The communications facilities provided by the communications module 120 include any one or a combination of at least the following:

LTE cellular communication Failover to satellite M2M communication;
Wi-Fi communication
TCP/IP LAN communication Power Module 130

The power module 130 may include any one, or any combination of two or more of the following power facilities/sources/inputs:

Drill rig fused 24 volt DC supply
Solar power 24 volt DC supply
Auxiliary power 220-240 volt AC or 110 volt AC supply
24 volt battery pack
Fuel cell
Wind turbine The power module also includes one or more power outlets or connectors to enable power supply to the powered components and sub-systems of the system 1. The outlet may supply power at the same or different voltages, current and frequencies. In the presently illustrated embodiment of the system 1 the power module 130 and the communications module 120 are shown as separate modules. However, in an alternate embodiment they can be housed in a common housing or case and transported or otherwise moved together and simultaneously coupled to other modules and subsystems of the system 1.

Portable Smart Device 140

The portable smart device 140 may include one or more of a local PC, tablet, or smart phone. The device 140 is connectable to the communications module 120 to enable communication with other components of the system one including the mud management system 10, the filtrate measurement system 70 and the mud dosing and mixing system 110. In this way for example data and other information from the systems 10, 70 and 110 can be viewed by an operator using a portable smart device 140 in say a cab of a drill rig or in an on-site hut. The operator may also use the portable smart device 142 issue commands to or otherwise control one of the systems 10, 70 and 110.

While embodiments of the disclosed system and method have been described above it would be apparent that other variations or modifications are possible. For example, the mud measurement system may incorporate additional or less measurement devices than those specifically described herein. Also, to assist in consistency of measurement results the mud measurement system may incorporate a mud sample temperature control facility arranged to heat or cool a sample of mud to a predetermined temperature prior to making measurements of the characteristics or properties of the mud. This may be particularly, but not exclusively, useful for measurements made on oil-based muds. Additionally or alternately, the system may be arranged to record the temperature of the mud at the time of making the measurements of its characteristics and properties.

Also, while the housing 12 as described above in one embodiment as being in the form of a shape and configuration of piece of check in luggage for an aircraft, the housing 12 may be in the form of a trailer that can be towed behind a mobile drill rig or other vehicle. Indeed, the mud management system 1 inclusive of the mud management system 10 is or can be a mobile system that is mounted on a trailer or powered vehicle. In one embodiment the entire mud management system comprising the mud measurement system 10, filtrate measurement system 70, mud dosing and mixing system 110, communications module 120, the power module 130, the supply of mud components/chemicals and supply of cleaning/flushing fluid 38 is a mobile and/or portable unit such as for example being mounted on a trailer or powered vehicle.

In the claims which follow and in the preceding description, except where the context requires otherwise due to express language or necessary implication, the word "comprise" and variations such as "comprises" or "comprising" are used in an inclusive sense, i.e. to specify the presence of the stated features but not to preclude the presence or addition of further features of the systems and methods as disclosed herein.

The invention claimed is:

1. An automated batch sampling drilling mud management system comprising:
   a portable mud measurement system having:
   one or more measurement devices arranged to measure at least one property and/or characteristic of drilling mud;
   a pumping system comprising:
   a reversible low-pressure, peristaltic, drilling mud pump arranged to pump a batch sample of drilling mud in a first direction from a supply of drilling mud to the one or more measurement devices and to subsequently operate in a reverse direction to flush the batch sample of drilling mud from the one or more measurement devices, said mud pump configured to apply a relative negative pressure to draw said mud into the one or more measurement devices; and
   a flushing fluid pump configured to introduce a flushing fluid into the one or more measurement devices; and
   a communications system enabling bidirectional communications between the mud management system and a remote location to enable transfer of data therebetween and the exertion of control from the remote location to the mud management system.

2. The mud management system of claim 1, wherein the mud measurement system is arranged to automatically issue a notification if at least one property or characteristic of the mud falls outside a desired specification.

3. The mud management system of claim 1, comprising a supply of a flushing fluid for delivery by the pumping system to the one or more measurement devices.

4. The mud management system of claim 1, wherein the pumping system is arranged to circulate mud from an external mud supply through a hose and back to the mud supply through a return pipe prior to delivering a batch sample of mud to the one or more measurement devices.

5. The mud management system of claim 1, wherein the pumping system is arranged to maintain a volume of the flushing fluid in contact with the one or more measurement devices after a measurement cycle in which the one or more measurement devices have measured the at least one property or characteristic of drilling mud.

6. The mud management system of claim 1, wherein the pumping system is arranged to run the flushing fluid pump to introduce a flushing fluid into the one or more measurement devices; and to subsequently operate the mud pump to empty the flushing fluid from the one or more measurement devices.

7. The mud management system of claim 1, wherein the pumping system comprises a valve connected between the mud pump, the return pipe and the one or more measurement devices, the valve having: a recycling state where the valve directs mud from the pump to flow only to the return pipe; and a flow-through state where the valve allows mud to flow from the pump to the at least one more measurement devices and blocks flow of mud to the return pipe.

8. The mud management system of claim 1, comprising a filtrate measurement system arranged to measure fluid loss of the drilling mud.

9. A method for measuring properties or characteristics of a drilling mud, said method comprising the steps of arranging an automated batch sampling drilling mud management system in accordance with claim 1 in fluid communication with an external mud supply, and measuring at least one property and/or characteristic of the drilling mud.

10. An automated, man-portable drilling mud measurement system as defined in claim 1 further comprising a housing sized and dimensioned to be carried as checked luggage on a commercial aircraft, said housing configured to contain the portable measurement system.

11. The mud management system of claim 1, comprising a mobile unit housing for carrying or housing the mud measurement system and the communication system, said housing sized to be carried as checked luggage on a commercial aircraft.

12. The mud management system of claim 11, wherein the mobile unit housing further carries or houses one or more of: the dosing system; the supply of one or more components or ingredients for dosing drilling mud; the supply of flushing fluid; and the filtrate system.

13. The mud management system of claim 1, comprising a dosing system arranged to, upon instruction from the mud measurement system or the communications system, automatically dose the drilling mud supply with one or more drilling mud ingredients on a basis of minimising differences between the measured at least one property or characteristic of the mud and a desired specification.

14. The mud management system of claim 13 comprising an interface to enable a local operator to enter data relating to a manual addition of one or more ingredients to the drilling mud supply and wherein the communications system is arranged to communicate the entered data to the remote location.

15. The mud management system of claim 13, which is arranged to provide feedback control in association with the dosing system and the mud measurement system by performing a test cycle on the mud after operation of the dosing system and to cause subsequent operations of the dosing system and the mud management system if the measurement devices indicate that the characteristics or properties of dosed mud lie outside the desired specification.

16. The mud management system of claim 13, comprising a supply of one or more components or ingredients for dosing drilling mud operatively associated with the dosing system.

17. The mud management system of claim 16, wherein the dosing system includes an inventory control system arranged to receive data relating to the supply of the one or more components or ingredients to facilitate ordering of additional components or ingredients.

18. An automated batch sampling drilling mud management system comprising:
a portable mud measurement system having:
one or more measurement devices arranged to measure at least one property and/or characteristic of drilling mud:
a pumping system comprising a single reversible mud pump having first and second ports and a first three-way valve connected between the first port, a supply of drilling mud and the one or more measurement devices whereby a batch sample of drilling mud is pumped operating in a first direction from the supply of drilling mud to the one or more measurement devices and subsequently operating in a reverse direction to flush the batch sample of drilling mud from the one or more measurement devices, said mud pump configured to apply a relative negative pressure to draw said mud into the one or more measurement devices; and a second three-way valve connected between the second port of the mud pump, the supply of drilling mud and a supply of flushing fluid whereby flushing fluid is introduced into the one or more measurement devices, the pumping system arranged to maintain a volume of the flushing fluid in contact with the one or more measurement devices after a measurement cycle in which the one or more measurement devices have measured the at least one property of characteristic of drilling mud; and
a communication system enabling bidirectional communications between the mud management system and a remote location to enable transfer of data therebetween and the exertion of control from the remote location to the mud management system.

* * * * *